(12) United States Patent
Toumazou et al.

(10) Patent No.: US 10,959,498 B2
(45) Date of Patent: Mar. 30, 2021

(54) WEARABLE DEVICE

(71) Applicant: DNANUDGE LIMITED, London (GB)

(72) Inventors: Christofer Toumazou, London (GB); Mohammadreza Sohbati, London (GB); Keren Hu, London (GB)

(73) Assignee: DNANUDGE LIMITED, London (GB)

( * ) Notice: Subject to any disclaimer, the term of this patent is extended or adjusted under 35 U.S.C. 154(b) by 0 days.

(21) Appl. No.: 16/645,241

(22) PCT Filed: Aug. 31, 2018

(86) PCT No.: PCT/GB2018/052480
§ 371 (c)(1),
(2) Date: Mar. 6, 2020

(87) PCT Pub. No.: WO2019/048835
PCT Pub. Date: Mar. 14, 2019

(65) Prior Publication Data
US 2020/0281331 A1    Sep. 10, 2020

(30) Foreign Application Priority Data

Sep. 6, 2017 (GB) .................................. 1714345.4

(51) Int. Cl.
*A44C 5/04* (2006.01)
*A44C 5/00* (2006.01)
(Continued)

(52) U.S. Cl.
CPC .............. *A44C 5/0007* (2013.01); *A44C 5/04* (2013.01); *A44C 5/06* (2013.01); *A44C 5/22* (2013.01); *A44D 2203/00* (2013.01); *A61B 5/681* (2013.01)

(58) Field of Classification Search
CPC .......... A44C 5/0007; A44C 5/04; A44C 5/06; A44C 5/22; A44C 5/14; A44C 5/00;
(Continued)

(56) References Cited

U.S. PATENT DOCUMENTS 2,448,943 A * 9/1948 Wolff ....................... A44C 5/14
224/168
2,558,007 A * 6/1951 Smith ................... A44C 5/0069
224/175
(Continued)

FOREIGN PATENT DOCUMENTS

| DE | 3508366 A1 | 12/1985 |
| EP | 0576998 A1 | 1/1994 |
| WO | 2014022907 A1 | 2/2014 |

OTHER PUBLICATIONS

International Search Report, dated Oct. 19, 2018, and Written Opinion issued in International Application No. PCT/GB2018/052480.
(Continued)

*Primary Examiner* — Jack W Lavinder
(74) *Attorney, Agent, or Firm* — Saul Ewing Arnstein & Lehr LLP (57) ABSTRACT

A wrist-worn device having the form of a continuous loop. The device comprises a plurality of elongate links, each link comprising at least one magnet, the links being connected to form a chain with neighbouring links being pivotable with respect to one another about a pivot axis that is substantially radial with respect to said loop. The magnets of neighbouring links have a respective positioning and polarity to provide an attractive force between the pair of neighbouring links when the pair of neighbouring links are in a side-by-side arrangement, whereby the chain of links has a first configuration in which the links are retained by the attractive
(Continued)

force in the side-by-side arrangement, and a second configuration of greater length than the first configuration.

8 Claims, 4 Drawing Sheets

(51) Int. Cl.
*A44C 5/06* (2006.01)
*A44C 5/22* (2006.01)
*A61B 5/00* (2006.01)

(58) Field of Classification Search
CPC ... A44D 2203/00; A61B 5/681; H01F 7/0263; Y10T 24/4782; Y10T 24/4718; Y10T 24/32; G04B 37/16
USPC .............................................. 63/5.1; 368/282
See application file for complete search history.

(56) References Cited

U.S. PATENT DOCUMENTS

| | | | |
|---|---|---|---|
| 3,885,383 A | 5/1975 | Tanaka | |
| 4,769,656 A * | 9/1988 | Dickey | H01Q 1/273 343/718 |
| 6,530,508 B1 * | 3/2003 | Devine | A45F 5/00 224/183 |
| 6,587,022 B1 | 7/2003 | Devine | |
| 9,615,543 B2 * | 4/2017 | Pach | A01K 1/04 |
| 2003/0230606 A1 | 12/2003 | Devinie | |
| 2013/0333418 A1 * | 12/2013 | Anger | A44C 5/0069 63/1.11 |

OTHER PUBLICATIONS

GB Combined Search and Examination Report, dated Mar. 9, 2018, issued in priority GB Application No. GB1714345.4.

* cited by examiner

WEARABLE DEVICE

CROSS REFERENCE TO RELATED APPLICATIONS

This application claims the priority of International Application No. PCT/GB2018/052480, filed on Aug. 31, 2018, which claims priority to GB Application No. 1714345.4, filed Sep. 6, 2017, the entire contents of which are fully incorporated herein by reference.

FIELD OF THE INVENTION

The present invention relates to a wearable device.

BACKGROUND OF THE INVENTION

Wearable devices are devices that can be worn on the body as accessories. In the field of wearable devices, connection structures that secure a device to a user's body typically include a loop for encircling a part of the user's body, and the loop is either selectively openable or (permanently) closed using a connection structure.

Openable connection structures connect two parts of a device that would typically not be connected when the device is not worn. An example of an open structure is where two ends of a strap are joined by a connecting buckle. Straps can be formed of flexible materials, such as leather, which are pleasant to wear for protracted periods. However buckles can be difficult to employ in use because they require both hands to operate.

Closed connection structures form a (permanently) closed loop, but some permit the circumference of the loop to be varied to allow the user to put the device on, so that the device can be worn. Examples of closed connection structures include bracelets, loops with butterfly buckles and loops formed with elastic materials.

A bracelet is a fixed size ring through which a user's wrist has to be forced. The bracelet diameter may be about the width of the user's palm, so bracelets can be difficult to put on but they stay loose on the wrist.

Butterfly buckles are typically used to connect links on stainless steel watchbands. However they have a complicated structure and it is difficult to adjust the length of the buckles without using specialist tools.

Loops formed of elastic materials, for example elastic rubber bands, conform to a user's body parts. However their elasticity decreases over time and they can be uncomfortable to wear. Elastic materials are therefore unsuitable for prolonged use of a wearable device. Furthermore, they are not easily compatible with cover layers of flexible material which is not sufficiently elastic to stretch as the circumference of the loop varies. For example, leather is incapable of stretching to such an extent.

It would therefore be desirable to have a more suitable wearable device, particularly for prolonged usage.

SUMMARY

The present invention aims to provide a wrist-worn device which is straightforward to put on with one hand and easily adjustable for different body part sizes. Moreover, the invention aims to provide a wrist-worn device that has a relatively slim profile in a radial direction.

According to a first aspect of the present invention there is provided a wrist-worn device having the form of a continuous loop. The device comprises a plurality of elongate links, each link comprising at least one magnet, the links being connected to form a chain with neighbouring links being pivotable with respect to one another about a pivot axis that is substantially radial with respect to said loop. The magnets of neighbouring links have a respective positioning and polarity to provide an attractive force between the pair of neighbouring links when the pair of neighbouring links are in a side-by-side arrangement, whereby the chain of links has a first configuration in which the links are retained by the attractive force in the side-by-side arrangement, and a second configuration of greater length than the first configuration.

The magnets may be surrounded by a cover layer which is of leather or synthetic leather. The cover layer may be a single continuous sleeve within which the magnets are located. When the chain of links is in the second, extended configuration, the sleeve is extended such that opposite poles of neighbouring magnets are spaced apart. When the chain of links is in the first, shortened configuration, the sleeve is concertinaed such that opposite poles of neighbouring magnets are in close proximity thereby retaining the chain in the first configuration.

The device may comprising an elongate strip of material having first and second ends to which said continuous sleeve is secured in order to form said continuous loop. The elongate strip of material may also be of a leather or synthetic leather material.

In general terms, the invention proposes a wrist-worn device having the form of a continuous loop and comprising links which are pairwise connected to form a chain. Neighbouring links are attracted together by magnets in each link, so that the chain of links can be put into a configuration in which the links are side-by-side. In this configuration, the chain has reduced overall length and it is maintained in this configuration by magnetic forces. Neighbouring links are pivotable with respect to one another about a pivot axis that is substantially radial with respect to the device when worn on a wrist.

Using such links provides an effective wrist-worn device that is straightforward to put on with one hand and easily adjustable for different body part sizes.

The links may be covered by a flexible cover layer of a material such as leather or synthetic leather, so that the chain of links is more comfortable to wear against the user's skin for a protracted period.

The links may include electrical contacts which conduct electricity between neighbouring links when the wrist-worn device is not being worn and the links are in the side-by-side arrangement. A long coil may thus be provided in the wrist-worn device that allows for effective wireless charging of the device.

The links may include multiple electrical contacts (and/or capacitive elements) that provide an electrical (and/or capacitive) connection directly between neighbouring links when the links are in the side-by-side arrangement, and an electrical pathway of different (e.g. higher) impedance when the links are not in the side-by-side arrangement. The impedance across the links may therefore be used to determine how many of the pairs of neighbouring links are side-by-side, which can provide an indication of information such as whether or not the device is being worn.

BRIEF DESCRIPTION OF THE DRAWINGS

Embodiments of the invention will now be described for the sake of example only, with reference to the following drawings in which:

FIG. 1, which is composed of FIGS. 1A, 1B and 1C, is a diagram of a wearable device which is an embodiment of the invention respectively in a first configuration, a second configuration and a third configuration;

DETAILED DESCRIPTION OF THE EMBODIMENTS

Referring firstly to FIG. 1, a wearable device 1 which is a first embodiment of the invention is shown including a plurality of elongate links 2 that are connected pairwise to form a chain. The term "elongate" means that the links have a greater extent in one direction than another direction, for example they may be have an extent at least twice, at least 3 times, at least 5 times or even at least 8 times as long in one direction as in another transverse direction. For example, the links may be rectangular or substantially rod-like in shape. Each link may be substantially rigid.

Each link 2 has two ends, and each end is attached to a different corresponding neighbouring link. The attachment is preferably permanent (i.e. it is not broken in typical use of the wearable device) but allows neighbouring links to rotate relative to each other in at least two dimensions. The attachment between neighbouring links may, for example, be provided by a hinge or a pivot between rigid elements of the respective links, and/or by a flexible cover layer surrounding the links and which extends from one link to the neighbouring link. It is particularly noted that the arrangement allows neighbouring links to pivot relative to one another about a pivot axis that extends substantially in a radial direction with respect to the band, where the radial direction is defined relative to an axis passing through the centre of the band and which is generally aligned when worn with the elongate extent of the wearer's wrist. This arrangement allows for a more compact or slim device in that radial direction. Moreover, the radial extent (that is the thickness of the band in that radial direction) is substantially unchanged regardless of whether the band is in the shortened collapsed configuration or in an extended configuration. This in in contrast to an arrangement in which the pivot axes extend parallel to the device axis, where the radial thickness of the band would be greater in the shortened configuration than in the extended configuration.

The wearable device 1 is shown in FIG. 1 in the form of a single continuous loop. In an alternative, the wearable device may be elongate, with respective ends for attachment to a common body so that a loop is formed collectively by the wearable device and the body. In this case the body may be an elongate strip of material, with the magnetic links being located within a continuous sleeve of a similar material and which is secured to both ends of the elongate strip, e.g. my clasps, screws, glue, etc, to form a closed loop. The magnetic links may be placed in sequence within the sleeve, with the sleeve forming a relatively tight fit around the links to prevent then sliding within the sleeve. Stitching may or may not be provided in the regions between neighbouring links.

The wearable device 1 is shown in FIG. 1 being worn on a user's wrist. The wearable device may be produced with a loop of a suitable circumference to fit around the wrists of a certain typical range of users. The wearable device 1 may further include a portion 11 that is not extendable, and that is connected at either end to respective ends of the chain of links, to form the loop. The portion 11 may for example be formed of plastic, fabric, silicone or leather.

Figure 1A:
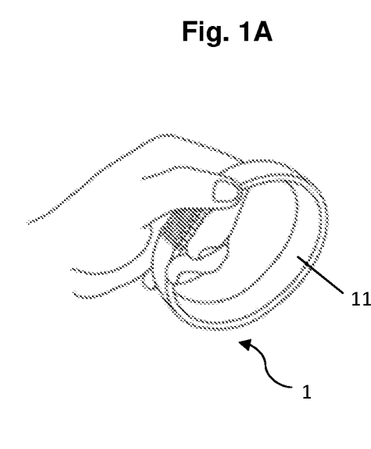
Figure 1B:
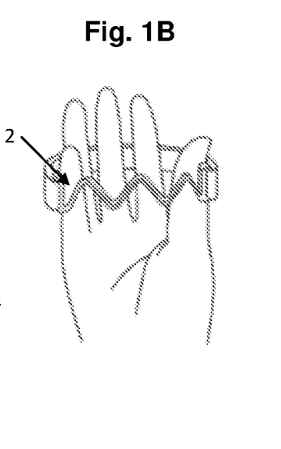
Figure 1C:
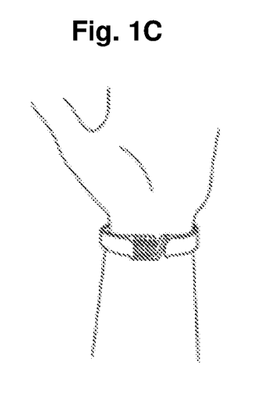

FIG. 1A shows the device in a first configuration, in which the links have a first "side-by-side" arrangement in which the respective length directions of the links are substantially parallel. In this configuration, the links are retained in a side-by-side arrangement by an attractive force (explained below). FIG. 1B shows the device in a second "extended" configuration, in which the links are not side by side, so that the length of the chain of links is extended, and so is the circumference of the device, so that the device is easily able to slide over a user's hand. FIG. 1C shows the device in a third "partially extended" configuration, in which some of the links 2 are in the side-by-side arrangement, and some are not, such that the device has a circumference intermediate between that of the first and second configurations.

Figure 2:
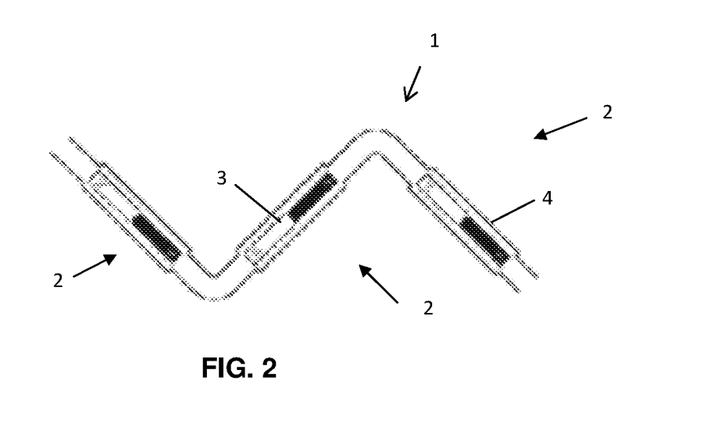
FIG. 2 is a cross-section through the links of the wearable device of FIG. 1.

FIG. 2 is a cross-sectional diagram of a part of the device 1 including three links 2. The attractive force is provided by at least one magnet 3 in each link. Each magnet 3 is surrounded by a flexible cover layer 4. The cover layer 4 extends substantially continuously along the entire length of the chain of links, surrounding the chain in the directions transverse to the length direction of the links. The magnets 3 of each pair of neighbouring links have a respective positioning and polarity to provide an attractive force between the pair of neighbouring links when the pair of neighbouring links are in a side-by-side arrangement. Specifically, consecutive links have respective magnets with alternating polarity, and in the side-by-side arrangement respective poles of each of the links are substantially in register in the length direction of the links with opposite poles of the two neighbouring links. One of the magnets 3 may be a magnetic battery.

The cover layer 4 may be any flexible material suitable for a wearable device, for example plastic, fabric or silicone. The cover layer 4 is preferably made of leather. The arrangement of the magnets and connected links in the wearable device allow the wearable device to be worn on a variety of body parts by users of different sizes, even if the cover layer 4 is not made of a stretchable material.

Figure 3:
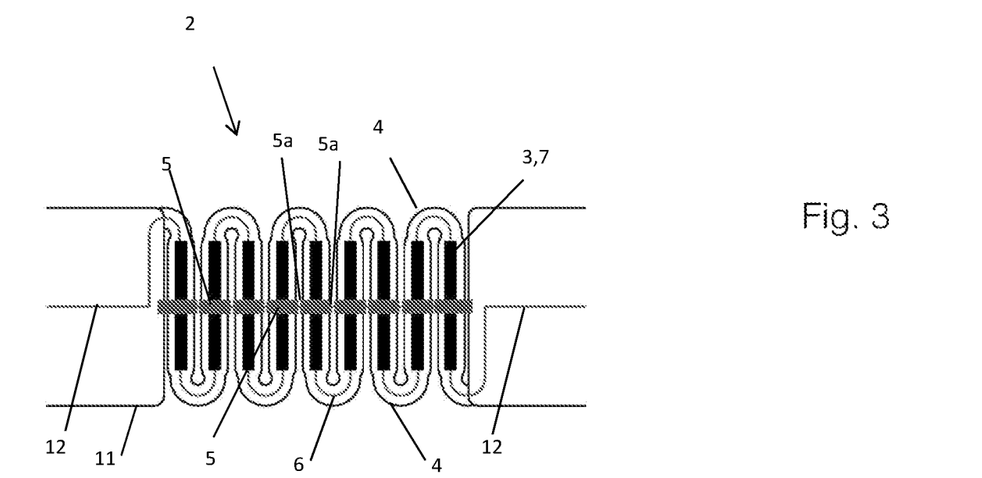
FIG. 3 is a schematic diagram of a wearable device which is a second embodiment of the invention, in a configuration with the links in a side-by-side arrangement.

FIG. 3 shows a wearable device which is a second embodiment of the invention. The second embodiment of the invention has the same external appearance and manner of use as illustrated in FIG. 1, and elements having the same meaning are designated by the same reference numerals. The first embodiment is illustrated in FIG. 3 in the "first configuration" of FIG. 1A, with the links in the side-by-side arrangement. The side-by-side link arrangement shown in FIG. 3 is typically a state the device adopts when the wearable device is not being worn by a user (i.e. the configuration of FIG. 1A). In contrast to the first embodiment, in the second embodiment each link 2 includes an elongate electrically conductive element 5 which extends transverse to the length direction of the link 2. Each end of the conductive element 5 penetrates through the cover layer 4, and forms a respective electrical contact 5a which is in register with a corresponding electrical contact 5a of the neighbouring link. Thus each pair of neighbouring links 2 in the device of FIG. 3 additionally includes at least two respective electrical contacts 5a which are in electrical contact when the pair of links lie side-by-side. The electrical contacts 5a are spaced from the parts of each link 2 that are connected to respective neighbouring links (as shown in FIGS. 2 and 3, this is the ends of the links). In the configuration shown in FIG. 3, the respective electrical contacts 5a of each pair of links 2 are touching because all of the links 2 are in a side-by-side arrangement. However, for ease of understanding, the links 2 are illustrated as being slightly spaced from each other in the horizontal direction of the diagram, with neighbouring contacts 5a slightly apart (which in reality they are not when the links are in the side-by-side arrangement).

Each of the pairs of neighbouring links 2 in the device of FIG. 3 also includes an electrical pathway between the electrical contact 5a of the conductive element 5 of one of the pair of links and the corresponding electrical contact 5a of the conductive element 5 of the other link of the pair of links. The electrical pathway includes a portion 6 at the connection between the pair of links. The electrical pathway, which may optionally include a resistor or other component, has a different impedance from the electrical connection between the electrical contacts 5a when the electrical contacts 5a touch. In the embodiment shown in FIG. 3, the impedance difference is provided by an impedance 7 in series with the electrical pathway. The impedance 7 may be, for example, a resistor and/or capacitor. Optionally, the impedance 7 may be provided by the magnetic elements 3, and thus the magnetic elements are not shown separately in FIG. 3.

The non-extendable portion 11 of the strap includes one or more embedded wires 12, which are electrically connected to the links 2 at the end of the chain, so that a circuit is formed. The wearable device of FIG. 3 may further include an impedance measuring unit (e.g. connected to the wires 12) configured to measure the impedance across the links (not shown in the figures). In the configuration shown in FIG. 3, all of the electrical contacts 5a of the neighbouring links 2 are touching. The electrical pathway between neighbouring links 2 is therefore through the electrical contacts and not through the impedance 7. Since the electrical contacts 5a have a lower impedance than the impedance 7, the side-by-side configuration shown in FIG. 3 therefore represents the lowest possible impedance across the links.

Figure 4:
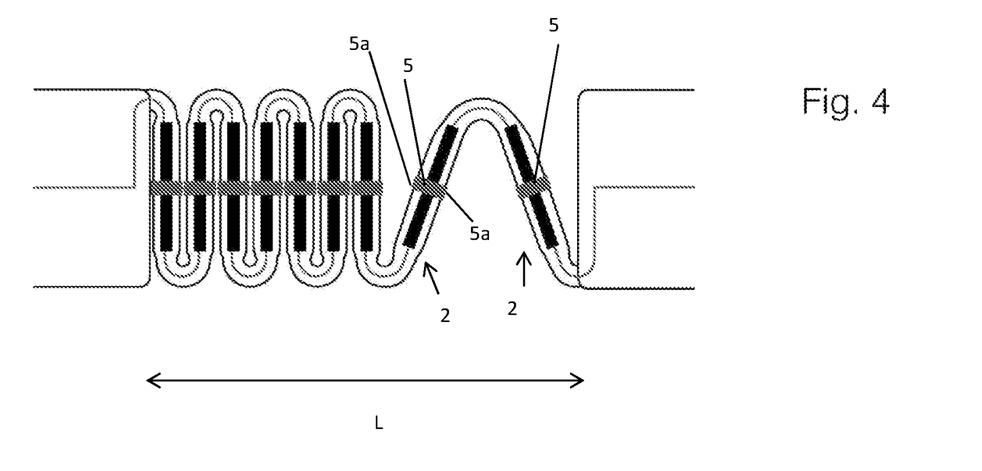
FIG. 4 is a schematic diagram of the wearable device of FIG. 3 with the links in a partially extended arrangement.

FIG. 4 shows the wearable device of FIG. 3 in a partially-extended configuration, which is a typical state when the wearable device is being worn and the circumference of the loop corresponds to that of the user's wrist. In the configuration of FIG. 4, two pairs of neighbouring links 2 have respective conductive elements 5 that are not touching. In this way, the electrical pathway through the neighbouring links with separated electrical contacts passes through the impedance 7 rather than the electrical contacts 5a. The partially-extended configuration of FIG. 4 thus results in a higher impedance across the links than the side-by-side link configuration of FIG. 3. The impedance across the links is a measure of the number of links that are not side-by-side, and thus the overall length L of the chain of links and the circumference of the wearable device 1. The impedance across the links increases with the overall circumference of the wearable device.

The wearable device may further include a processor connected to the impedance measuring unit, and arranged to determine, based on the impedance measured by the impedance measuring unit, whether the wearable device is currently being worn. The determination can be made on the basis that where the measured impedance across the links is at a minimum, all of the links are touching and so the device is not being worn. When the device is being worn, at least one pair of links will not be touching, and so the impedance across the links will be greater than when the device is not being worn. The processor may further use the measured impedance between the links to determine the circumference of the wearable device, since the number of unconnected electrical contacts is representative of the number of links that that are not side-by-side. The circumference of the user's body part on which the wearable device is worn may be measured over time. In this way the wearable device may be used to track, for example, user physiological changes such as weight loss. The processor may use the determined circumference of the wearable device to determine on which part of the body the wearable device is being worn by a user. For example, the processor may determine that the wearable device is being worn on the user's wrist, palm, neck, finger, foot or leg. Based on the determination of the worn location, the processor may turn a connected computing module on or off. The processor may be provided on a printed circuit board (PCB), optionally with other components. It may be a simple microcontroller, or a more powerful processor. For example, the processor may be enabled to control and/or receive images from a camera provided in the wearable device, and the microprocessor may also be capable of performing image processing.

Note that in a variation of the second embodiment, the conductive elements 5 may be replaced with respective capacitive elements (which optionally are entirely within the cover 4). The corresponding capacitive elements of neighbouring links interact capacitatively with each other when the links are in the side-by-side arrangement. Thus, again, the impedance of the chain of links depends upon whether neighbouring links are side-by-side.

Figure 5:
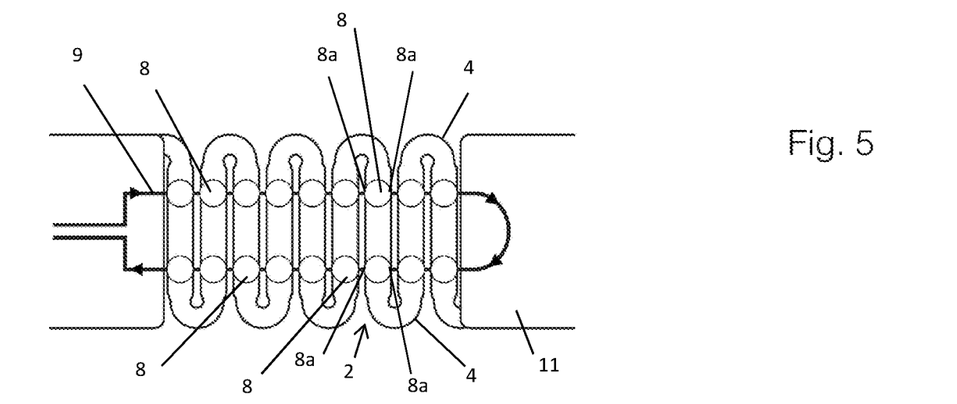
FIG. 5 is a schematic diagram of a wearable device which is a third embodiment of the invention with the links in a side-by-side arrangement.

FIG. 5 shows a wearable device which is a third embodiment of the invention, with the links in a side-by-side arrangement. Again, elements having the same meaning as in the first embodiment are designated by the same reference numeral. As in the first embodiment each link 2 includes a magnetic element, but in FIG. 5 the magnetic elements are omitted for simplicity. The third embodiment of the invention has the same external appearance and manner of use as illustrated in FIG. 1. The side-by-side arrangement represents a state in which the wearable device is not being worn. Each of the pairs of neighbouring links 2 in the device of FIG. 3 include at least two conductive elements 8 which penetrate the cover 4 to either lateral side of the link, to provide at least four electrical contacts 8a per link (i.e. two per conductive element 8) where the conductive elements 8 are exposed. The electrical contacts 8a of the third embodiment function in the same way as the electrical contacts 5a of the second embodiment. However unlike the second embodiment, there is no electrical pathway including a portion at the connection between the pair of links, with a different impedance from the electrical connection between the conductive elements 5 when the first electrical contacts 5a touch. Instead, the neighbouring links in the third embodiment are only electrically connected to one another by the electrical contacts 8a, and only when the neighbouring links are side-by-side. For ease of understanding, in FIG. 5 the conductive elements 8 of neighbouring links are shown slightly spaced from each other, but in reality in the first configuration the conductive elements 8 of neighbouring links touch.

The configuration of electrical contacts in the third embodiment form part of an inductive coil 9 when the wearable device is in the first configuration (i.e. the links are all in the side-by-side arrangement). When any pair of the links is not in the first arrangement, the coil 9 is interrupted.

Figure 8:
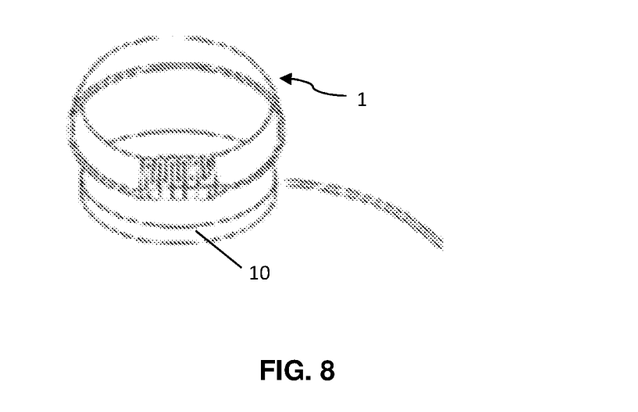
FIG. 8 is a diagram illustrating charging of a wearable device which is one of the embodiments of the invention.

The wearable device of FIG. 5 may further include a charging unit (not shown). The charging unit may be connected (typically electrically, although it is alternatively possible that the connection is inductive) to the coil 9 when the links are in the side-by-side arrangement. Alternatively, the charging unit may be connected to a coil loop that extends through the connection portion between at least one pair of links, the coil loop not being interrupted in any configuration of the wearable device. The charging unit may be located in the portion 11. The charging unit is preferably a wireless charging unit such as an inductive charging unit. The inductive charging unit is charged when a current flows in the inductive coil 9 due to time-variations in a magnetic field applied to the wearable device from outside. In this way the coil may be used to charge the wearable device when the wearable device is placed near a charging station 10 using electromagnetic (e.g. wireless) radiation. Such a configuration is shown in FIG. 8. An easy to charge wearable device may thus be provided.

Figure 6:
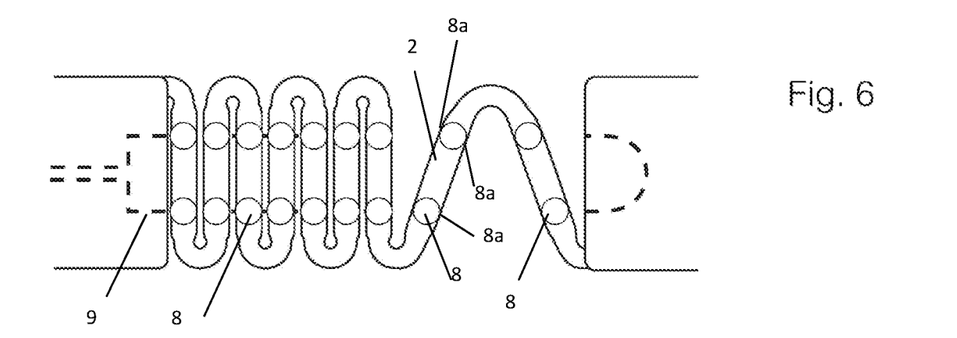
FIG. 6 is a schematic diagram of the wearable device of FIG. 5 with the links in a partially extended arrangement.

FIG. 6 shows the wearable device of FIG. 5 in a partially-extended configuration, representing a state in which the wearable device is being worn. In the configuration of FIG. 6, at least one pair of neighbouring links has electrical contacts 8a that are not touching. The coil 9 is thus interrupted, and the charging of the wearable device is interrupted also. The arrangement of FIGS. 5 and 6 permits the area of the wearable device which receives the electromagnetic radiation in the first configuration to be increased without increasing the size of the device. Where provided, the charging unit may be configured to detect when the inductive coil is interrupted. The detection may be based on measurements of the impedance of the coil.

Figure 7:
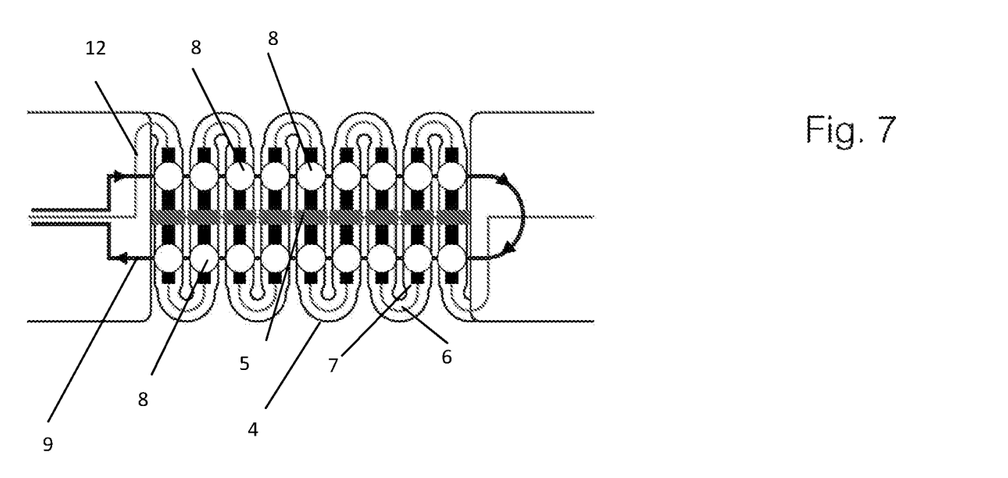
FIG. 7 is a schematic diagram of a wearable device which is a fourth embodiment of the invention with the links in a side-by-side arrangement.

FIG. 7 shows a wearable device which is a fourth embodiment of the invention, which again has the same outer appearance and manner of use as the first embodiment. Again, corresponding elements are designated by the same reference numerals. In FIG. 7 the fourth embodiment of the wearable device is illustrated with the links in a side-by-side arrangement. The fourth embodiment is a combination of the second and third embodiments, in that it includes both conductive elements and impedance elements corresponding to the conductive elements 5 and impedance elements 7 of the second embodiment, and conductive elements and coil elements corresponding to the conductive elements 8 and the inductive coil 9 of the third embodiment.

The wearable devices of any of the disclosed embodiments may further include a communication unit arranged to communicate with external devices. The communication unit may use one or more of the following communication technologies: Bluetooth, WiFi, EDGE, 3GPP, HSDPA, LTE, 5G. The communication unit may be located in the portion 11.

The wearable devices of any of the disclosed embodiments may further include an output unit, and a control unit for sensing the presence of an item outside the wearable device. The output unit and/or control unit may be located in the portion 11. Upon sensing the presence of the item, the control unit may cause the output unit to issue an alert.

The control unit may also measure one or more of the following: user DNA, user heart rate, user blood oxygenation, user blood glucose and user temperature. The control unit may also cause the output unit to issue an alert in response to data received from an external device via the communication unit. The external device may be, for example, a database containing the user's DNA and associated potential genetic health issues. The external data may be, for example, user-specific purchasing recommendations based on the user's DNA profile and potential genetic health issues. Alternatively the wearable device may receive portions of the user's DNA and analyse the received DNA to provide genetically optimised purchasing recommendations. In this way the wearable device can alert a user to specific goods, such as foods, that may be particularly beneficial to an individual user based on their DNA.

The output unit may provide audible, visual or tactile notifications to the user. For example, the notification unit may be a display or LED. The notification unit may be configured to provide notifications to the user based on data measured by the control unit. The notification unit may, for example, notify the user when the user's vital signs are outside a particular range.

The wearable devices of any of the disclosed embodiments may, in the first configuration (i.e. when the links are all in the side-by-side arrangement), have a circumferential length in the configuration of FIG. 1A in the range 20 mm to 250 mm, and more preferably in the range 100 mm to 200 mm.

Whilst the foregoing description has described exemplary embodiments, it will be understood by those skilled in the art that many variations of the embodiment can be made within the scope and spirit of the present invention.

The invention claimed is:

1. A wrist-worn device having the form of a continuous loop, comprising:
   a plurality of elongate links, each link comprising at least one magnet surrounded by a cover layer, the links being connected pairwise to form a chain with neighbouring links being pivotable with respect to one another about a pivot axis that is substantially radial with respect to the device when worn on a wrist;
   the magnets of each pair of neighbouring links having a respective positioning and polarity to provide an attractive force between the pair of neighbouring links when the pair of neighbouring links are in a side-by-side arrangement;
   whereby the chain of links has a first configuration in which the links are retained by the attractive force in the side-by-side arrangement, and a second configuration of greater length than the first configuration.

2. The wearable device of claim 1, in which the cover layer is leather.

3. The wearable device of claim 1, further comprising at least two electrical contacts on each pair of neighbouring links,
   the electrical contacts including, for each pair of neighbouring links, a first electrical contact on one of the pair of links positioned to touch a corresponding second electrical contact of the other of the pair of links when the two links are side-by-side, the first and second electrical contacts being spaced from respective parts of each of the pair of links that are connected.

4. The wearable device of claim 1, further comprising at least one capacitive element in each link for forming a capacitive interaction with the capacitive element of the neighbouring link when the pair of links are in the side-by-side arrangement.

5. The wearable device of claim 1, further comprising, for each pair of neighbouring links, an electrical pathway between one of the pair of links and the other link of the pair of links, the electrical pathway including a portion at the connection between the pair of links.

6. The wearable device of claim 1, further comprising an impedance measuring unit configured to measure the impedance across the links.

7. The wearable device of claim 6 further comprising a processor arranged to determine based on the impedance whether the wearable device is currently being worn.

8. The wearable device according to claim 1 which, when the chain is in the first configuration, has a length in the range 20 mm to 250 mm.

* * * * *